US012678436B2

(12) United States Patent
Lee et al.

(10) Patent No.: US 12,678,436 B2
(45) Date of Patent: Jul. 14, 2026

(54) PHARMACEUTICAL COMPOSITION FOR PREVENTING OR TREATING FIBROSIS

(71) Applicant: Daewoong Pharmaceutical Co., Ltd., Gyeonggi-do (KR)

(72) Inventors: Caroline Hee Lee, Seoul (KR); Min Jae Cho, Seoul (KR); Min Young Park, Seoul (KR); Ju Mi Han, Seoul (KR); Joon Seok Park, Seoul (KR)

(73) Assignee: Daewoong Pharmaceutical Co., Ltd., Gyeonggi-do (KR)

( * ) Notice: Subject to any disclaimer, the term of this patent is extended or adjusted under 35 U.S.C. 154(b) by 364 days.

(21) Appl. No.: 18/288,296

(22) PCT Filed: May 2, 2022

(86) PCT No.: PCT/KR2022/006230
§ 371 (c)(1),
(2) Date: Oct. 25, 2023

(87) PCT Pub. No.: WO2022/240035
PCT Pub. Date: Nov. 17, 2022

(65) Prior Publication Data

US 2024/0216363 A1 Jul. 4, 2024

(30) Foreign Application Priority Data

May 13, 2021 (KR) ........................ 10-2021-0062252
Aug. 20, 2021 (KR) ........................ 10-2021-0110520

(51) Int. Cl.
*A61K 31/496* (2006.01)
*A61K 31/4418* (2006.01)
(Continued)

(52) U.S. Cl.
CPC ........ *A61K 31/496* (2013.01); *A61K 31/4418* (2013.01); *A61K 31/454* (2013.01); *A61P 11/00* (2018.01)

(58) Field of Classification Search
CPC .............. A61K 31/496; A61K 31/4418; A61K 31/454; A61K 2300/00; A61P 11/00; A61P 43/00
(Continued)

(56) References Cited

U.S. PATENT DOCUMENTS

| | | | |
|---|---|---|---|
| 10,981,917 | B2 | 4/2021 | Lee et al. |
| 2019/0282565 | A1 | 9/2019 | Liang |

(Continued)

FOREIGN PATENT DOCUMENTS

| | | | |
|---|---|---|---|
| CL | 2019002019 | A1 | 12/2019 |
| CN | 112469406 | A | 3/2021 |

(Continued)

OTHER PUBLICATIONS

Flaherty et al., "Safety of Nintedanib Added to Pirfenidone Treatment for Idiopathic Pulmonary Fibrosis", Eur Respir J, 2018, V. 52(2):1800230, [online], [found May 27, 2024]. Found in PubMed, PMID: 29946005, doi: 10.1183/13993003.00230-2018, abstract, 10 pages.

(Continued)

*Primary Examiner* — Taylor V Oh
(74) *Attorney, Agent, or Firm* — MARSHALL, GERSTEIN & BORUN LLP

(57) ABSTRACT

The pharmaceutical composition according to the present invention is used at specific therapeutic regimen and dosage, and can be usefully used for the prevention or treatment of fibrosis.

6 Claims, 10 Drawing Sheets

(51) Int. Cl.
*A61K 31/454* (2006.01)
*A61P 11/00* (2006.01)

(58) Field of Classification Search
USPC ..................................................... 514/254.01
See application file for complete search history.

(56) References Cited

U.S. PATENT DOCUMENTS

| | | | |
|---|---|---|---|
| 2019/0359617 A1 | 11/2019 | Lee et al. |
| 2021/0205253 A1 | 7/2021 | Song et al. |
| 2024/0216363 A1 | 7/2024 | Lee et al. |
| 2024/0307365 A1 | 9/2024 | Lee et al. |

FOREIGN PATENT DOCUMENTS

| | | | |
|---|---|---|---|
| JP | 2020-506197 A | 2/2020 |
| KR | 102084772 B1 | 3/2020 |
| RU | 2733384 C1 | 10/2020 |
| WO | WO-2010/018134 A1 | 2/2010 |
| WO | WO-2018/147626 A1 | 8/2018 |
| WO | WO-2019/183006 A1 | 9/2019 |
| WO | WO-2019/231281 A1 | 12/2019 |

OTHER PUBLICATIONS

Lee et al., "Synergistic Anti-Fibrotic Effect of a First-in-Class PRS Inhibitor, DWN12088, and Standard-of-Care Therapeutic Agents for IPF", Am J Respir Crit Care Med, 2021, V. 203, Online Abstracts Issue, A4645, publ. May 3, 202. [online], [found May 27, 2024], 1 page.
Dhooria et al., A Real-world Study of the Dosing and Tolerability of Pirfenidone and its Effect on Survival in Idiopathic Pulmonary Fibrosis. Sarcoidosis Vasc Diffuse Lung Dis, 2020, V. 37(2), pp. 148-157, [online], [found May 27, 2024]. Found in PubMed, PMID: 33093778, doi: 10.36141/svdld.v37i2.8718, c. 149, right column, last paragraph.
Flaherty et al., "Nintedanib in Progressive Fibrosing Interstitial Lung Diseases", The New England Journal of Medicine, 2019, V. 381, N. 18, pp. 1718-1727, [online], [found May 27, 2024]. Found in PubMed, PMID: 31566307, DOI: 10.1056/NEJMoa1908681, Abstract, Trial Treatment.
Office Action in RU Application No. 2023123353/04(051422) dated May 29, 2024, 18 pages.
Office Action in RU Application No. 2023122618/04(049669) dated May 13, 2024, 18 pages.
Kim et al., "Recent Development of Aminoacyl-tRNA Synthetase Inhibitors for Human Diseases: A Future Perspective", Biomolecules, vol. 10, 1625, 2020, 24 pages.
Lee et al., "A First-in-Class PRS Inhibitor, DWN12088, as a Novel Therapeutic Agent for Idiopathic Pulmonary Fibrosis", B20 Therapeutics "2020" in Lung Disease, Mini Symposium, Am J Respir Crit Care Med, 2020, 3 pages.
Henderson et al., "Fibrosis: From Mechanisms to Medicines", Nature, vol. 587 (7835), Nov. 25, 2020, pp. 555-566.
Lee et al., "Inhibition of Prolyl-tRNA Synthetase as a Novel Therapeutic Target for Systemic Sclerosis", Meeting: 2018 ACR/ARHP Annual Meeting, Oct. 21, 2018, Abstract No. 128, 3 pages.
Park et al., "Inhibition of Prolyl-tRNA Synthetase as a Novel Mediator of Cardiac Fibrosis", 2017 Late-Breaking Basic Science Oral Abstracts I, Circulation, 2017, vol. 136, 10 pages.
Office Action in Saudi Arabian Application No. 523450897 dated Nov. 21, 2024, 8 pages.
Office Action in JP Application No. 2023-567149 dated Dec. 24, 2024, 13 pages.
Lee et al., "A First-in-Class PRS Inhibitor, DWN12088, as a Novel Therapeutic Agent for Idiopathic Pulmonary Fibrosis", In: Therapeutics "2020" in Lung Disease, Mini Symposium, American Journal of Respiratory and Critical Care Medicine, Article No. A2786, vol. 201, 2020, 2 pages.
Song et al., "Glutamyl-Prolyl-tRNA Synthetase Regulates Epithelial Expression of Mesenchymal Markers and Extracellular Matrix Proteins: Implications for Idiopathic Pulmonary Fibrosis", Frontiers in Pharmacology, vol. 9, Article 1337, Nov. 2018, 11 pages.
Zhou et al., "ATP-Directed Capture of Bioactive Herbal-Based Medicine on Human tRNA Synthetase", Nature, vol. 494, 2013, pp. 121-125.
Kim et al., "Aminoacyl-tRNA Synthetases and Tumorigenesis: More Than Housekeeping", Nat. Rev. Cancer, vol. 11, Oct. 2011, pp. 708-718.
Hübner et al., "Standardized Quantification of Pulmonary Fibrosis in Histological Samples", BioTechniques, vol. 44, No. 4, 2008, 9 pages.
Search Report in International Application No. PCT/KR2022/006230 dated Aug. 10, 2022, 8 pages.
Lee et al., "Synergistic Anti-Fibrotic Effect of a First-in-Class PRS Inhibitor, DWN12088, and Standard-of-Care Therapeutic Agents for IPF", 2019 IPF Summit, Sheraton San Diego Hotel & Marina, CA, Aug. 28, 2019 1 page.
Lee et al., "A First-in-Class PRS Inhibitor, DWN12088, As a Novel Therapeutic Agent for Idiopathic Pulmonary Fibrosis", Am J Respir Crit Care Med 2021, 203:A4645, May 2021, 1 page.
Abstract Supplement 2018 ACR/ARHP Annual Meeting, Arthritis & Rheumatology, John Wiley & Sons, Inc, US, vol. 70, Oct. 15, 2018 (Oct. 15, 2018), Abstract 128, pp. 136-137, XP072276985.
Kreuter et al., "Pharmacological Treatment of Idiopathic Pulmonary Fibrosis: Current Approaches, Unsolved Issues, and Future Perspectives", BioMed Research International 2015.1, 2015: 329481, 10 pages.
Extended European Search Report in EP Application No. 22807683.2 dated Apr. 8, 2025, 8 pages.
Office Action in CL Application No. 202303345 dated Feb. 28, 2025, 18 pages.
Office Action in Saudi Arabian Application No. 523450746 dated Mar. 26, 2025, 7 pages.
Clinical Trials, To Evaluate Drug-drug Interactions Between DWN12088 and Pirfenidone or Nintedanib in Healthy Volunteers, [online], NCT04888 715, May 11, 2021, [Accessed: Sep. 2, 2025], Source <https://clinicaltrials.gov/study/NCT04888715?tab=history&a=1#version-content-panel>, 9 pages.
Notice of Allowance in JP Application No. 2023-567150 dated Nov. 3, 2025, 8 pages.
Park et al., "Safety, Tolerability and Pharmacokinetics/Pharmacodynamic Assessment of an Oral, Selective Prolyl-tRNA Synthetase Inhibitor, DWN12088, for the Treatment of Idiopathic Pulmonary Fibrosis in Healthy Subjects", Am J Respir Crit Care Med, 203:A1897, 2021, 1 page.
Office Action in CN Application No. 202280033307.4 dated Dec. 17, 2025, 8 pages.
Office Action in CN Application No. 202280034620.X dated Jan. 5, 2026, 9 pages.
Gan et al., "Comparison of in-vitro anti-fibrotic effects of pirfenidone and nintedanib", Chinese Pharmacological Bulletin, vol. 35(10), 2019, 6 pages.
Office Action in TW Application No. 111118048 dated Dec. 8, 2025, 12 pages.
Park et al., "Aminoacyl tRNA synthetases and their connections to disease", Proc. Natl. Acad. Sci., vol. 105 (32), 2008, pp. 11043-11049.
Adachi et al., "Biochemical and Biophysical Research Communications", Biochemical and Biophysical Research Communications, vol. 488, Issue 2, 2017, pp. 393-399.
Li et al., "Functional analysis of keratinocyte and fibroblast gene expression in skin and keloid scar tissue based on deviation analysis of dynamic capabilities", Exp Ther Med, vol. 12 (6), 2016, pp. 3633-3641.
Floreani et al., "Treatment of primary sclerosing cholangitis", Digestive and Liver Disease, vol. 53, 2021, pp. 1531-1538.
Andreas Stahl, "The diagnosis and treatment of age-related macular degeneration", Dtsch Arztebl Int., vol. 117 (29-30), 2020, pp. 513-520.

(56) References Cited

OTHER PUBLICATIONS

Shibata et al., “Discovery and pharmacological characterization of a new class of prolyl-tRNA synthetase inhibitor for anti-fibrosis therapy”, PloS One, vol. 12 (10), 2017, 17 pages.
King et al., “A phase 3 trial of pirfenidone in patients with idiopathic pulmonary fibrosis”, New England Journal of Medicine, vol. 370, No. 22, 2014, pp. 2083-2092.
Richeldi et al., “Efficacy and safety of nintedanib in idiopathic pulmonary fibrosis”, New England Journal of Medicine, vol. 370, IS22, 2014, pp. 2071-2082.
Flaherty et al., “Safety of nintedanib added to pirfenidone treatment for idiopathic pulmonary fibrosis”, Eur Respir J, vol. 52, 2018, 11 pages.
Wang et al., “Mathematical modeling in cancer drug discovery”, Drug Discovery Today, vol. 19, Issue 2, 2014, pp. 145-150.

[FIG. 1]
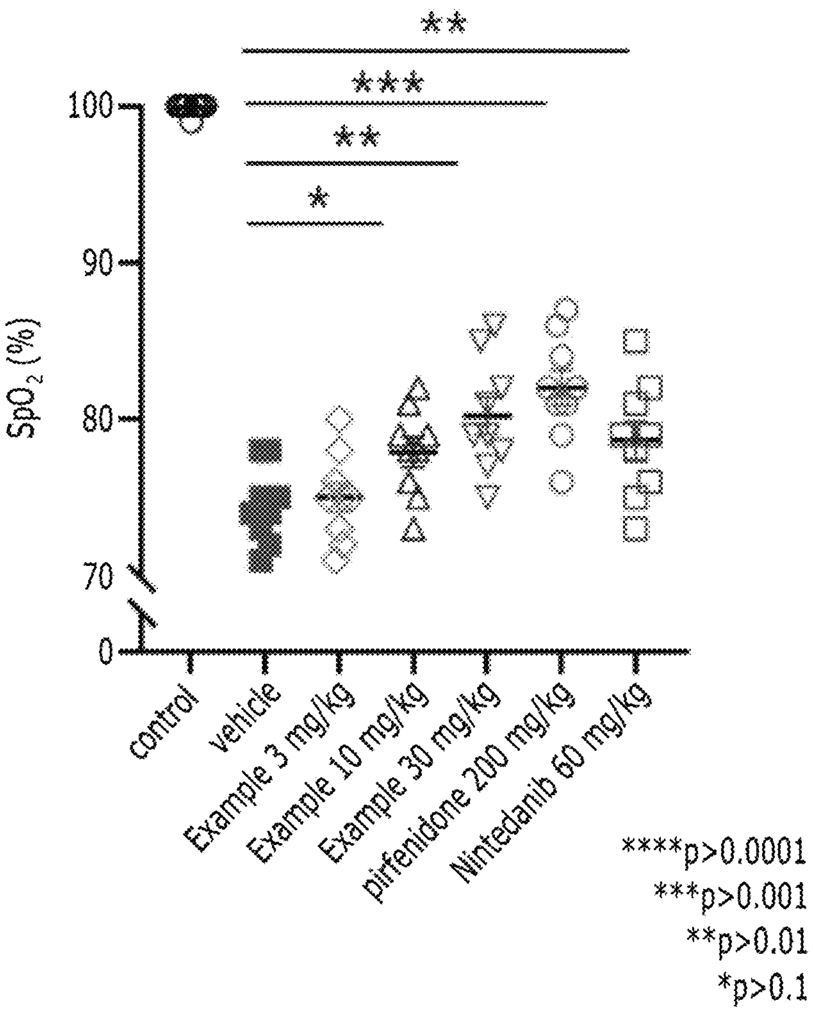

[FIG. 2]
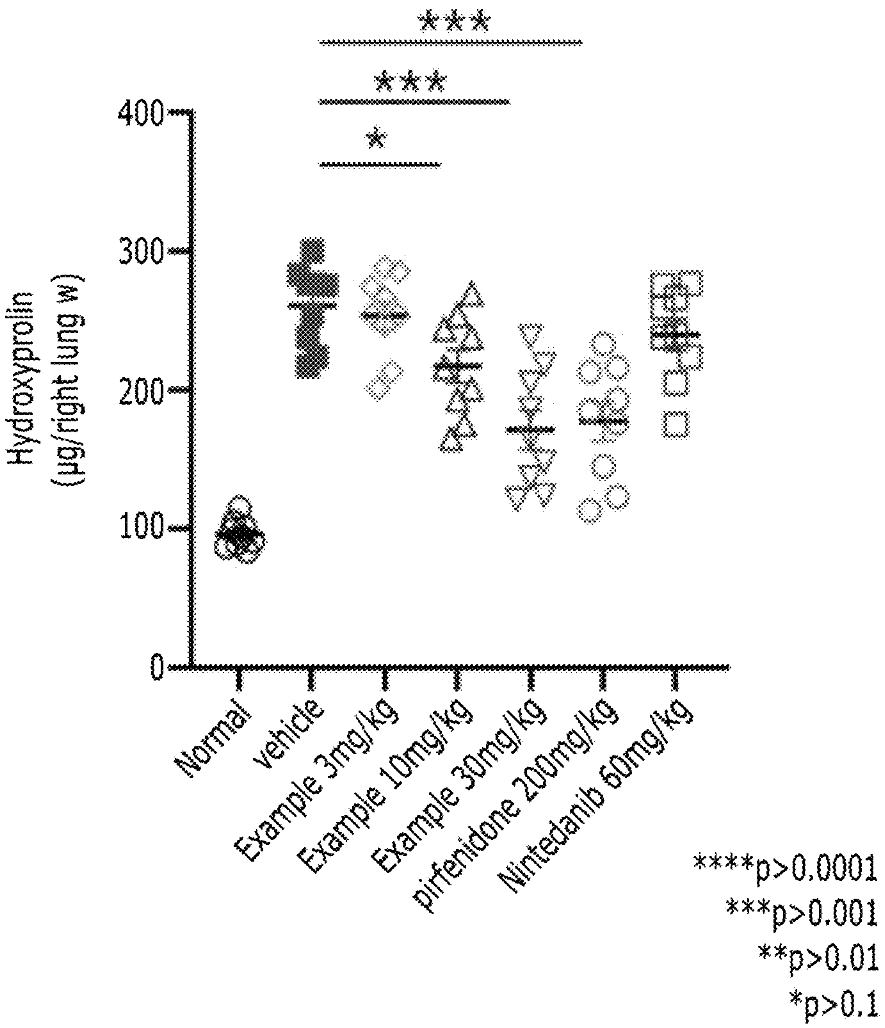

[FIG. 3]
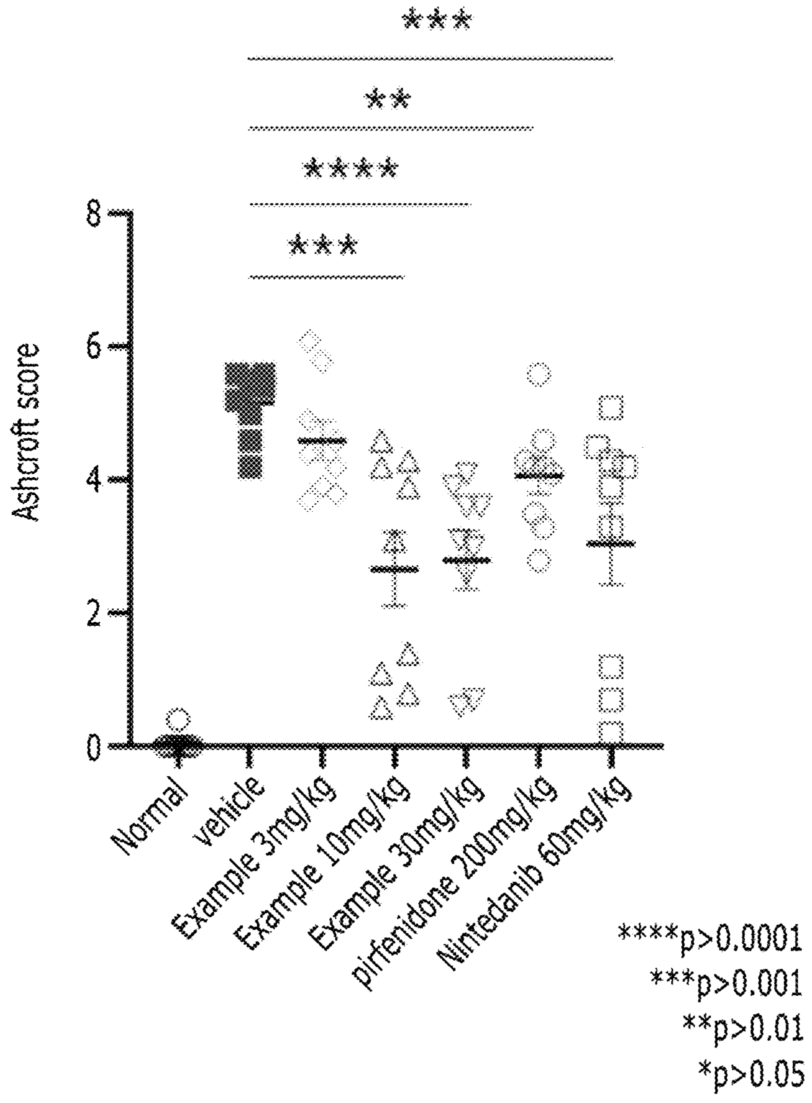

[FIG. 4]
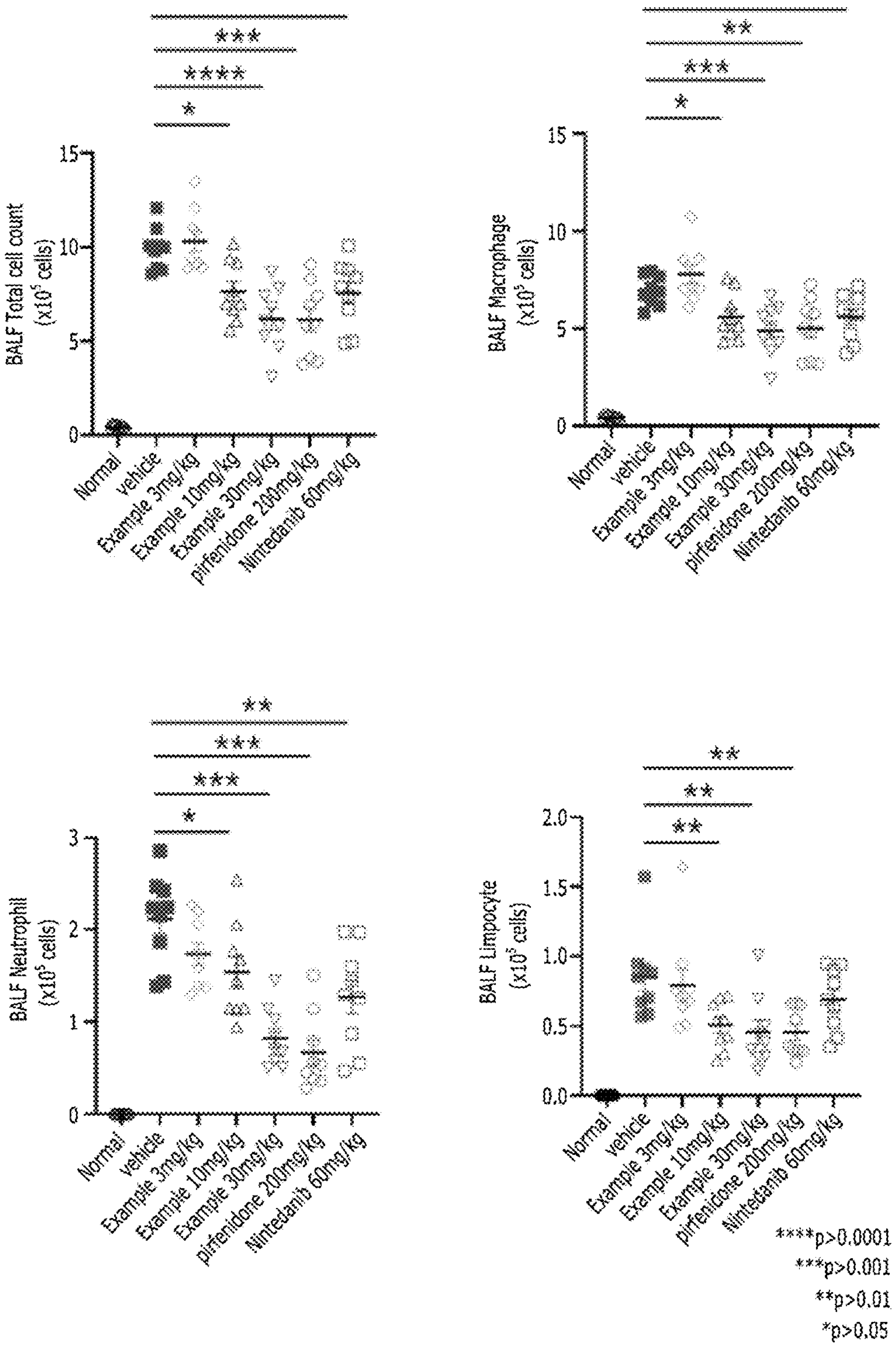

[FIG. 5]
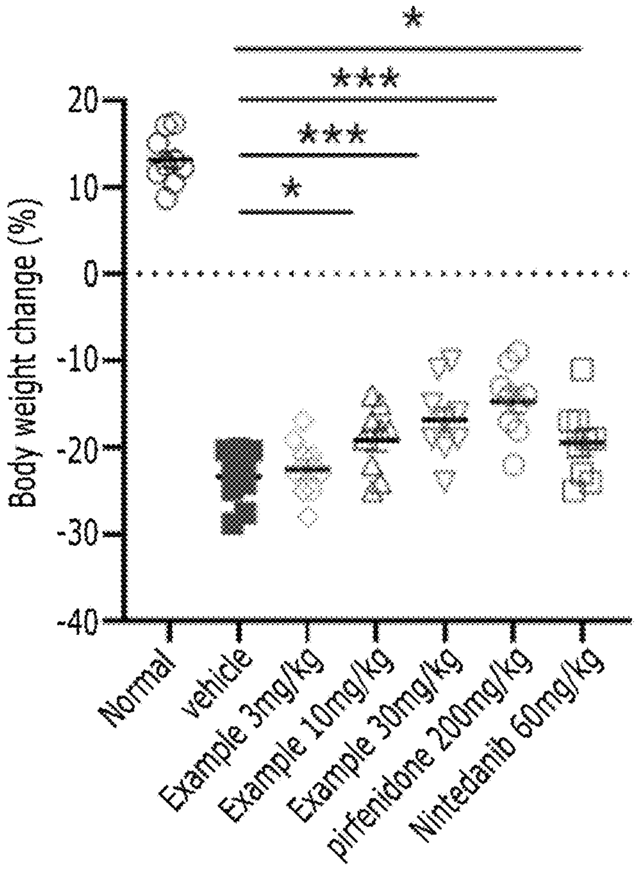
****p>0.0001
***p>0.001
**p>0.01
*p>0.05

[FIG. 6]
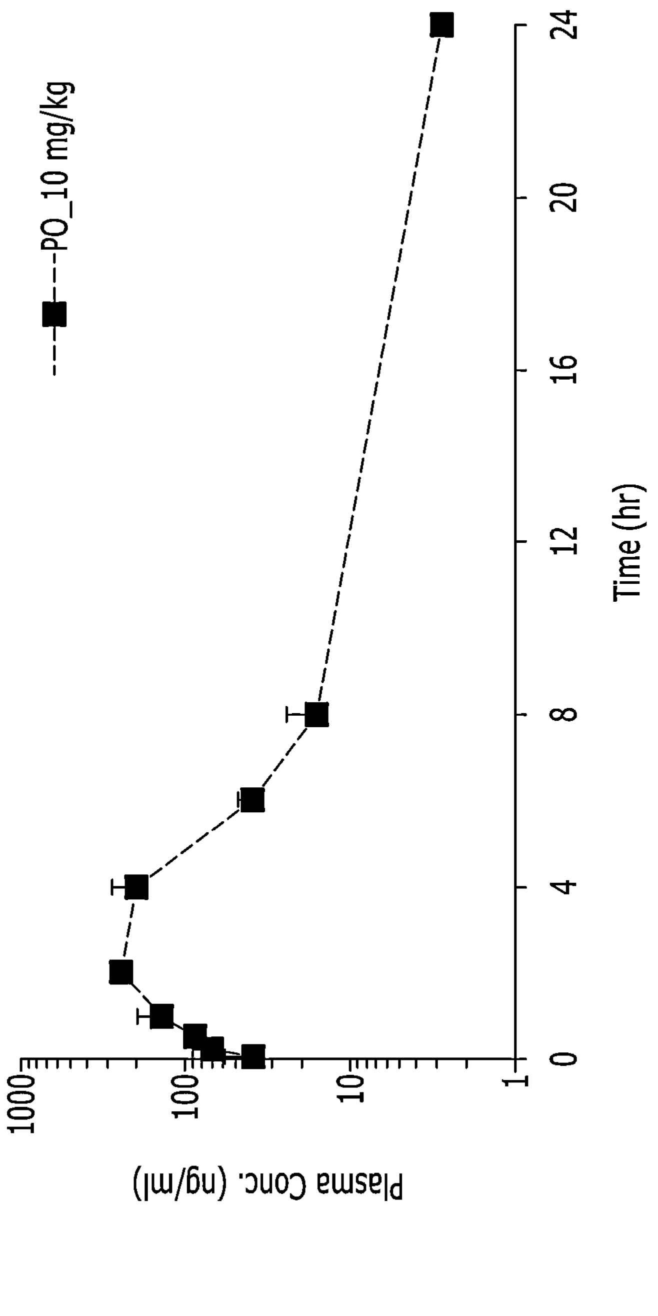

[FIG. 7]
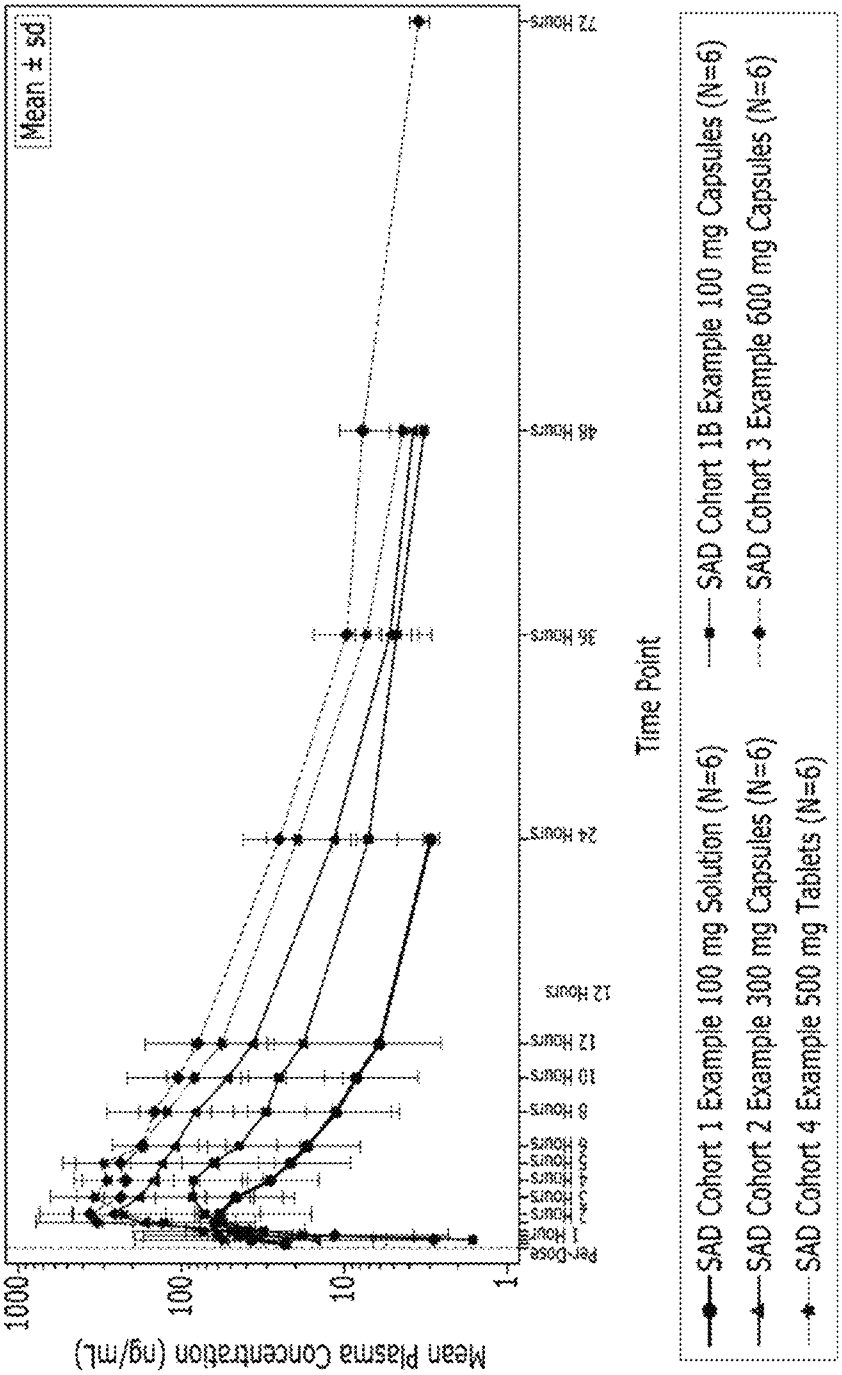

[FIG. 8]
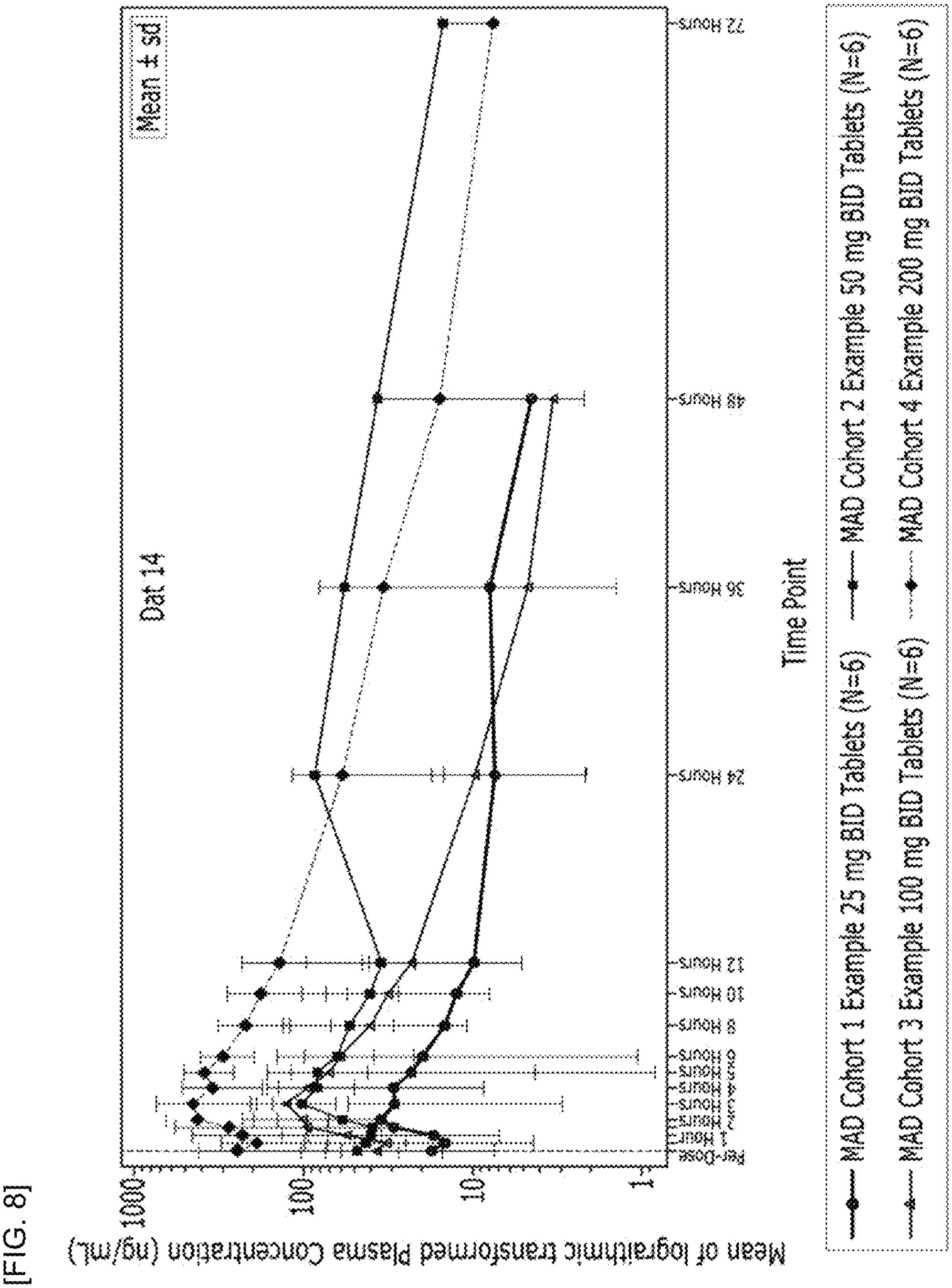

[FIG. 9]
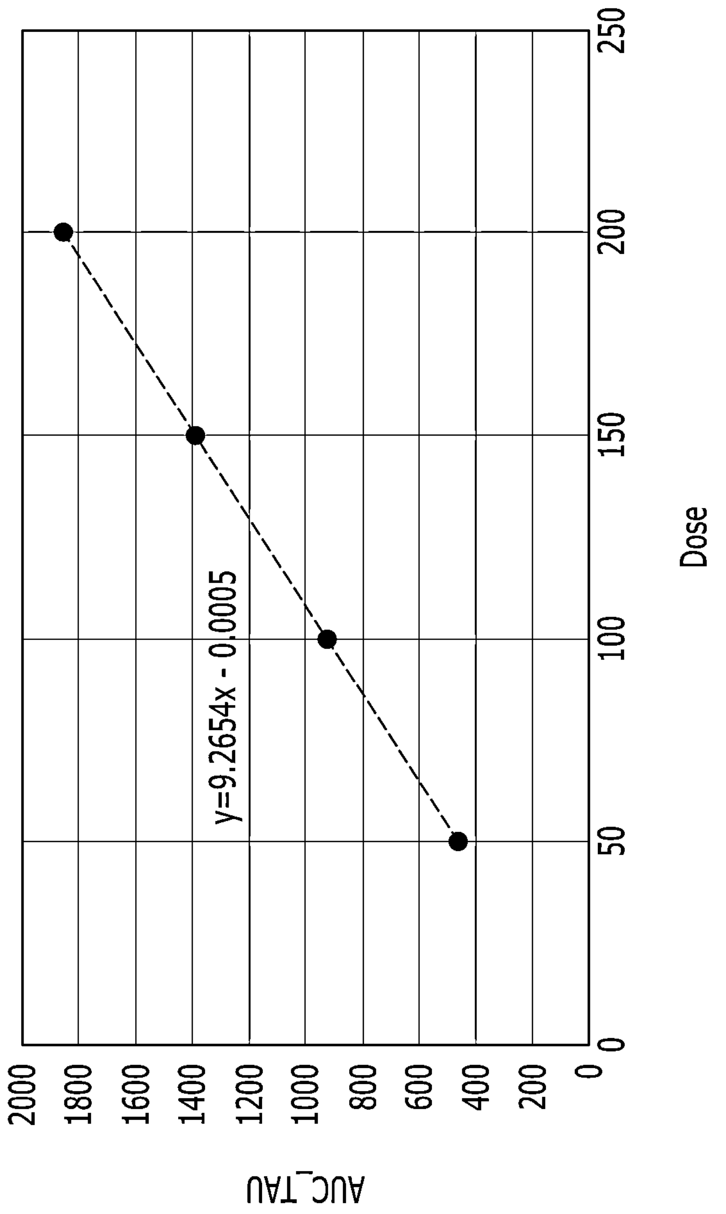

[FIG. 10]
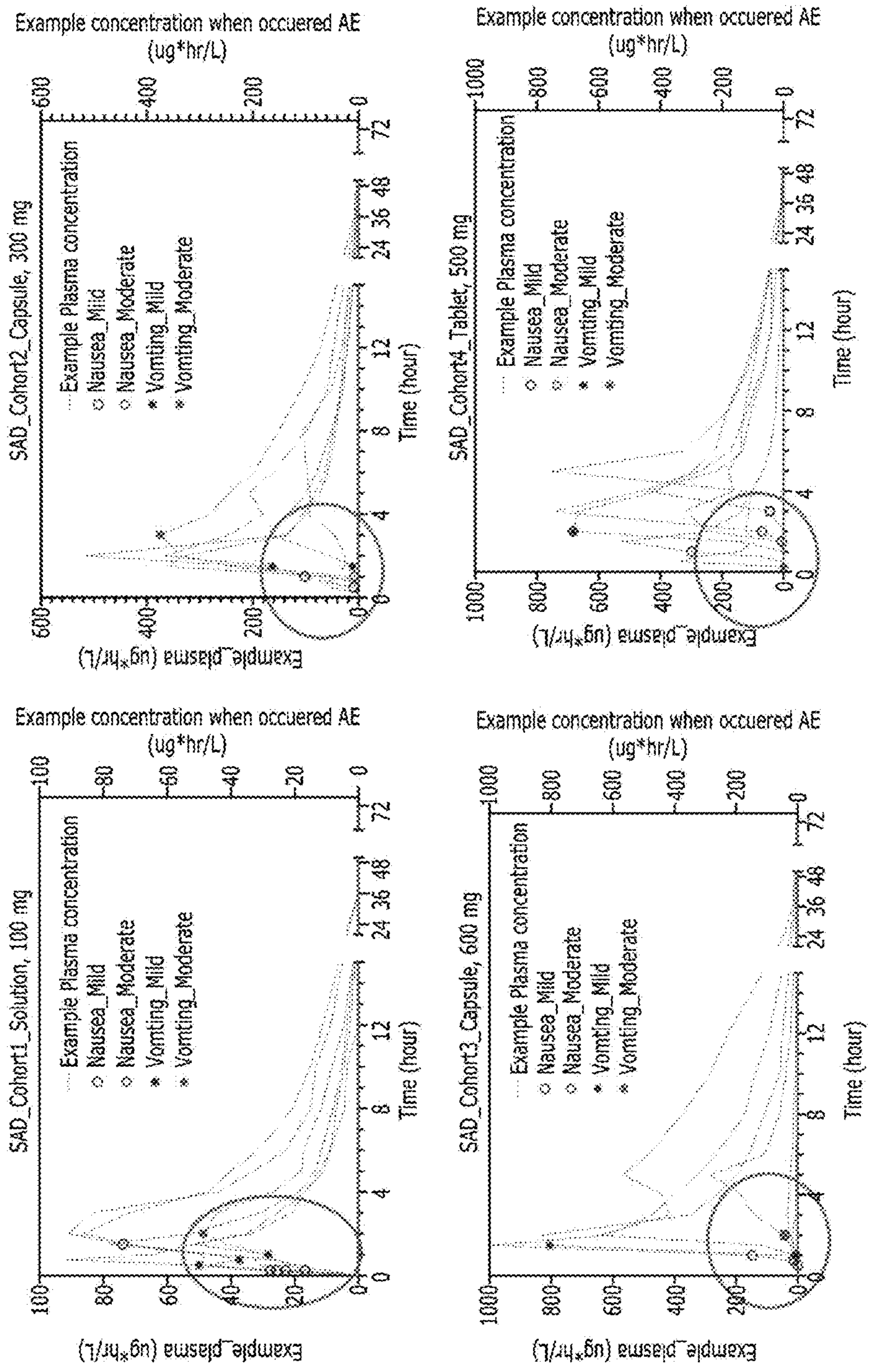

PHARMACEUTICAL COMPOSITION FOR PREVENTING OR TREATING FIBROSIS

TECHNICAL FIELD

The present disclosure relates to a pharmaceutical composition for preventing or treating fibrosis.

BACKGROUND ART

Fibrosis refers to a phenomenon in which part of an organ stiffens for some reason, and pulmonary fibrosis or liver fibrosis is considered a typical disease. In the case of pulmonary fibrosis, it is almost predominant that the lungs stiffen due to radiation exposure or filling the lungs with water. However, pulmonary fibrosis may occur in only some people. There are almost no complete therapeutic method for fibrosis symptoms to date, and therapeutic methods are being developed and studied. Types of fibrosis include interstitial lung disease (ILD), Scleroderma, Keloid, Hypertrophic scar, Non-alcoholic Fatty Liver Disease, Primary sclerosing cholangitis (PSC), primary biliary cholangitis (PBC), diabetic retinopathy, Age-related Macular Degeneration (AMD), hypertrophic cardiomyopathy, myocardial infarction, Muscular Dystrophy, Diabetic kidney disease, focal segmental glomerulosclerosis (FSGS), Inflammatory bowel disease (IBD), and the like. Interstitial lung disease includes idiopathic pulmonary fibrosis (IPF), systemic sclerosis associated interstitial lung disease (SSc-ILD), and chronic fibrosing interstitial lung diseases with a progressive phenotype (PF-ILD), and the like.

Idiopathic pulmonary fibrosis (IPF) is one of the chronically progressive interstitial lung diseases, which falls under a rare disease, and it is known that the course of the disease is not good and proven therapeutic method does not exist. Until now, the cause has not been clearly proved, and the 5-year survival rate after diagnosis is 43%, and the 10-year survival rate is about 15%, which is not good. Although many studies are being conducted, there is no therapeutic method that improves the survival rate so far. Considering that other interstitial lung diseases, such as non-specific interstitial pneumonia (NSIP) and idiopathic organized pneumonia (COP), have a relatively good outcome when properly treated, it can be said that the course of the disease is poor among the interstitial lung diseases. The most common causes of death are respiratory failure (39%) and heart disease (27%), and others include lung cancer, pulmonary embolism, and pneumonia. The prognosis is worse if the patient is elderly or male poor, or if lung function is poor at the time of diagnosis or there are many fibroblastic foci in the biopsy.

Similar to non-specific interstitial pneumonia (NSIP), the therapeutic method for idiopathic pulmonary fibrosis uses steroids and cytotoxic drugs. Recently, anti-fibrotic agents are the main therapeutic method, and various attempts have been made. Currently approved drugs for idiopathic pulmonary fibrosis include Pirfenidone and Nintedanib, and these drugs are not a complete therapeutic agent, but they act to delay pulmonary fibrosis and relieve symptoms. Therefore, there is a need to develop more effective drugs that can improve the patient's quality of life.

Systemic sclerosis associated interstitial lung disease (SSc-ILD) is a disease that has interstitial lung disease (ILD) as a complication among patients with systemic sclerosis (SSc), and deterioration in lung function is the leading cause of death in systemic sclerosis. As a therapeutic agent approved for the disease in the United States, there are Nintedanib and Tocilizumab, which have confirmed the effect of reducing deterioration in pulmonary function, but there is a need to develop more effective drugs that can improve the patient's quality of life, similarly to idiopathic pulmonary fibrosis.

Chronic fibrosing interstitial lung diseases with a progressive phenotype (PF-ILD) refers to various progressive fibrosing interstitial lung diseases except idiopathic pulmonary fibrosis, which includes autoimmune interstitial lung disease, idiopathic interstitial pneumonia, and the like. Nintedanib has been confirmed to have the effect of reducing the deterioration in pulmonary function in patients with various fibrotic lung diseases and has been approved as a therapeutic agent in the United States. Since fibrotic interstitial lung diseases can develop a progressive phenotype such as pulmonary fibrosis, deterioration in lung function, and poor quality of life, the effect of reducing the deterioration in lung function can be expected even in other interstitial lung diseases when the effect of reducing the deterioration in pulmonary function in specific interstitial lung disease is demonstrated regardless of classification and underlying disease.

Meanwhile, PRS (prolyl-tRNA synthetase) is one of the aminoacyl-tRNA synthetase (ARS) family, and serves to activate amino acids for protein synthesis. That is, ARS performs a translational function to form aminoacyl adenylate (AA-AMP) and then transfer the activated amino acid to the third end of the corresponding tRNA. Because ARS plays a key role in protein synthesis, ARS inhibition inhibits the growth and growth of all cells. Therefore, ARS is recognized as a promising target for antibiotics or therapeutic agents for diseases that must suppress cell overexpression (Nature, 2013, 494: 121-125).

PRS is present in, or functions as, a multisynthetase complex (MSC) in the form of Glutamyl-Prolyl-tRNA Synthetase (EPRS). Particularly, among various MSCs, EPRS functions as a transcriptional silencer that suppresses the production of vascular endothelial growth factor A (VEGF A), which is a key factor in angiogenesis. In addition, it has been reported that EPRS is closely related with various solid cancers (Nat. Rev. Cancer, 2011, 11, 708-718).

Therefore, the present inventors intensively studied methods for preventing or treating fibrosis, and confirmed that effective prevention or treatment of fibrosis is possible when a specific PRS inhibitor, which will be described later, is used at specific therapeutic regimen and dosage, thereby completing the present invention.

DETAILED DESCRIPTION OF THE INVENTION

Technical Problem

It is an object of the invention to provide a pharmaceutical composition for preventing or treating fibrosis.

Technical Solution

In order to achieve the above object, there is provided a pharmaceutical composition for preventing or treating fibrosis as follows:

A pharmaceutical composition for preventing or treating fibrosis, comprising a compound represented by the following Chemical Formula 1 for administrating 100 to 150 mg twice a day (BID), or a pharmaceutically acceptable salt thereof.

[Chemical Formula 1]

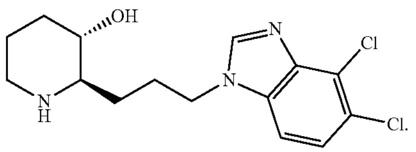

A compound represented by Chemical Formula 1, or a pharmaceutically acceptable salt thereof is a compound described in Korean Patent Registration No. 10-2084772, and specifically a substance described in Example 40 of the specification. The substance can be used as a PRS inhibitor for the prevention or treatment of fibrosis.

In particular, when administering 100 to 150 mg twice a day (BID) as in the present invention, effective prevention or treatment of fibrosis is possible. The above dosage is a dosage that can prevent potential risks to the maximum extent while increasing the preventive or therapeutic effect on fibrosis of the compound represented by Chemical Formula 1, or a pharmaceutically acceptable salt thereof. Further, depending on the dosage, the plasma drug concentration-time curve area (AUCinf) after administration of the compound represented by Chemical Formula 1, or a pharmaceutically acceptable salt thereof, that is, the exposure to the body can show optimal results for the prevention or treatment of fibrosis.

Meanwhile, the compound represented by Chemical Formula 1 may be used in the form of a pharmaceutically acceptable salt. As salt, an acid addition salt formed by a pharmaceutically acceptable free acid is useful. As the free acid, an inorganic acid and an organic acid may be used. Examples of the inorganic acid may include hydrochloric acid, bromic acid, sulfuric acid, phosphoric acid, and the like. Examples of the organic acid may include citric acid, acetic acid, lactic acid, maleic acid, gluconic acid, methanesulfonic acid, succinic acid, 4-toluene sulfonic acid, glutamic acid, aspartic acid or the like. Preferably, the pharmaceutically acceptable salt of the compounds represented by Chemical Formula 1 is hydrochloride.

Further, the compound represented by Chemical Formula 1 can be prepared in crystalline form or non-crystalline form. When the compound represented by Chemical Formula 1 is produced in crystalline form, it may be optionally hydrated or solvated. The present invention may include not only stoichiometric hydrates of the compound represented by Chemical Formula 1 but also compounds containing a various amount of water. The solvates of the compound represented by Chemical Formula 1 include both stoichiometric solvates and non-stoichiometric solvates.

Meanwhile, examples of the fibrosis include Interstitial lung disease (ILD), Scleroderma, Keloid, Hypertrophic scar, Non-alcoholic Fatty Liver Disease, Primary sclerosing cholangitis (PSC), primary biliary cholangitis (PBC), diabetic retinopathy, Age-related Macular Degeneration (AMD), hypertrophic cardiomyopathy, myocardial infarction, Muscular Dystrophy, Diabetic kidney disease, focal segmental glomerulosclerosis (FSGS), or Inflammatory bowel disease (IBD). The Interstitial lung disease (ILD) includes idiopathic pulmonary fibrosis (IPF), systemic sclerosis associated interstitial lung disease (SSc-ILD), or chronic fibrosing interstitial lung diseases with a progressive phenotype (PF-ILD).

The term "prevention" as used herein refers to any act to delay or inhibit occurrence, spread or recurrence of a cancer, an inflammatory disease, an autoimmune disease or a fibrosis by administration of the composition of the present invention, and "treatment" refers to any act to improve or change the symptoms of the above diseases for the better by administration of the composition of the present invention.

The pharmaceutical composition according to the present invention can be formulated in types for oral or parenteral administrations according to a standard pharmaceutical practice. These formulations may contain additives such as pharmaceutically acceptable carrier, adjuvant or diluent in addition to the active component.

Suitable carriers include, for example, physiological saline, polyethylene glycol, ethanol, vegetable oil, and isopropyl myristate and the like. Diluents include, for example, lactose, dextrose, sucrose, mannitol, sorbitol, cellulose and/or glycine and the like, but are not limited thereto. Further, the compounds of the present invention can be dissolved in oils, propylene glycol or other solvents commonly used in the preparation of injection solutions. Furthermore, the compounds of the present invention can be formulated in ointments or creams for topical application.

The pharmaceutical dosage forms of the compounds of the present invention can also be used in the form of a pharmaceutically acceptable salt or solvate thereof, and they can be used alone or in combination with other pharmaceutically active compounds, as well as in appropriate association. In one example, the pharmaceutical composition according to the present invention may further include other active components used for the prevention or treatment of fibrosis. Examples of such other active components include Pirfenidone or Nintedanib. Additionally, when the pharmaceutical composition according to the present invention further comprises other active component, the weight ratio of the compound represented by Chemical Formula 1, or a pharmaceutically acceptable salt thereof, and the other active component is preferably 1:0.1 to 1:10.

The compounds of the present invention can be formulated into injections by dissolving, suspending or emulsifying the compounds in aqueous solvents such as common physiological saline or 5% dextrin, or in non-aqueous solvents such as synthetic fatty acid glycerides, higher fatty acid esters or propylene glycol. The formulation of the present invention may include conventional additives such as solubilizers, isotonic agents, suspending agents, emulsifying agents, stabilizers and preservatives.

The pharmaceutical composition according to the present invention may be administered via oral or parenteral routes. Depending on the method of administration, the composition according to the present invention may contain 0.001 to 99% by weight, preferably 0.01 to 60% by weight of the compound represented by Chemical Formula 1, or a pharmaceutically acceptable salt thereof.

The pharmaceutical composition according to the present invention may be administered to mammals such as a rat, a mouse, a domestic animal, a human, through various routes. The administration may be carried out through all possible methods, for example, oral, rectal, intravenous, intramuscular, subcutaneous, intra-endometrial, intracerebroventricular injection.

Advantageous Effects

As described above, the pharmaceutical composition according to the present invention is used at specific therapeutic regimen and dosage, and can be usefully used for the prevention or treatment of fibrosis.

BRIEF DESCRIPTION OF THE DRAWINGS

FIG. 1 shows the results of the lung function evaluation of Experimental Example 1-1.

FIG. 2 shows the results of measurement of the collagen content inside the lungs of Experimental Example 1-2.

FIG. 3 shows the results of the histopathological analysis of Experimental Examples 1-3.

FIG. 4 shows the results of the inflammatory cell infiltration analysis of Experimental Example 1-4.

FIG. 5 shows the results of the weight change measurement of Experimental Examples 1-5.

FIG. 6 shows the change in blood concentration of the active component of Experimental Example 3.

FIG. 7 shows the change in plasma concentration for a single administration of Experimental Example 4.

FIG. 8 shows changes in plasma concentration for multiple administrations of Experimental Example 4.

FIG. 9 is a graph showing the correlation with the AUC according to the dose administered in Experimental Example 4.

FIG. 10 shows the relationship between the time of occurrence of side effects of nausea and vomiting and exposure to the body in Experimental Example 5.

DETAILED DESCRIPTION OF THE EMBODIMENTS

Below, the present invention will be described in more detail by way of examples. However, these examples are provided for illustrative purposes only, and should not be construed as limiting the scope of the present invention to these examples.

EXAMPLE

The following compound was prepared in the same manner as in Example 40 of Korean Patent Registration No. 10-2084772, and was hereinafter referred to as 'active component' or 'Example'.

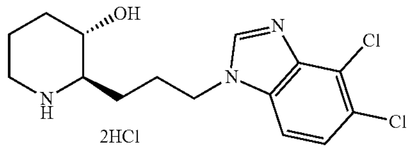 [SMILES: O[C@H]1CCCN[C@@H]1CCCn1cnc2c(Cl)c(Cl)ccc21]

$^1H$ NMR (500 MHZ, MeOD): δ 9.67 (s, 1H). 8.02 (d, 1H), 7.82 (d, 1H), 4.62 (m, 2H), 3.60 (m, 1H), 3.28 (m, 1H), 2.99 (m, 2H), 2.25 (m, 2H), 2.08 (m, 2H), 1.99 (m, 1H), 1.78 (m, 2H), 1.54 (m, 1H)

Experimental Example 1: Animal Experiment of Anti-Fibrotic Efficacy by Dose 70-100 μL of BLM solution (bleomycin 1-3 mg/kg) was administered to a lung of the acclimatized experimental animals using a catheter for 5 days or more. In accordance with the purpose of the test, the test drug was administered 7 days after BLM administration, and the drug was orally administered for 2 weeks until the 21st day of BLM administration. The composition of the experimental group is as shown in Table 1 below. Body weight, SpO2, hydroxyproline, and inflammation cell counts were measured to determine the anti-fibrotic efficacy of the active component.

As a control group, Nintedanib (hereinafter 'NIN') and Pirfenidone (hereinafter 'PID'), which are standard of care (hereinafter 'SoC') for idiopathic pulmonary fibrosis, were used. The effective dose of NIN used was confirmed through in vivo efficacy data in the literature published by Boehringer Ingelheim, which is a NIN development company, and the effective dose of PID was set in terms of mice based on in vivo efficacy (rat) data and 2-week repeated toxicity dose (rat) in FDA Pharmacology Review.

TABLE 1

| Group | Drug | No of Animals (Male) | Dose 1 (mg/kg) | Dose 2 (mg/kg) (SoC) | Volume (μL) | Method of administration |
|---|---|---|---|---|---|---|
| G1(NC) | Saline | 9 | N/A | N/A | 100 | Oral |
| G2(PC) | Saline | 9 | N/A | N/A | 100 | Oral |
| G3(Test) | Active component | 9 | 3 | N/A | 100 | Oral |
| G4(Test) | Active component | 9 | 10 | N/A | 100 | Oral |
| G5(Test) | Active component | 9 | 30 | N/A | 100 | Oral |
| G6(Test) | Nintedanib | 9 | N/A | 60 | 100 | Oral |
| G7(Test) | Pirfenidone | 9 | N/A | 200 | 100 | Oral |

Experimental Example 1-1: Lung Function Evaluation

This lung function evaluation is the most direct and important evaluation index that has the greatest influence on the symptoms and quality of life of patients with pulmonary fibrosis, and is an experiment that can most directly show the effect of improving lung function in an animal model of pulmonary fibrosis by measuring the oxygen concentration in the body.

On the 21st day, it was measured with a SpO2 measuring device (Berry, Veterinary Pulse Oximeter) via the abdominal side of the mouse, and the results are shown in Table 2 and FIG. 1.

An attempt was made to confirm the oxygen permeation function of the lungs through SpO2 measurement in the abdomen of a mice. It was confirmed that compared with Vehicle, the function was improved by 18% or more at 10 mg/kg of 'active component' and by 28% or more at 30 mg/kg. It was confirmed that this was the same degree of improvement in oxygen permeation function as the existing SoC material. This is a result confirming that there was a direct improving effect on lung function when 'active component' was administered through an increase in oxygen permeability, which was reduced in the process of pulmonary fibrosis.

TABLE 2

| | | Active component | | | Pirfenidone | Nintedanib |
|---|---|---|---|---|---|---|
| Normal | Vehicle | 3 mg/kg | 10 mg/kg | 30 mg/kg | 200 mg/kg | 60 mg/kg |
| 99.89 | 74.44 | 75.00 | 77.89 | 81.33 | 82.00 | 78.67 |

Experimental Example 1-2: Measurement of Total Collagen Content in Lung

Pulmonary fibrosis is the accumulation of collagen in the lungs to make it stiff. The main cause of pulmonary fibrosis is the accumulation of collagen, and the degree of progression of fibrosis can be predicted by measuring the collagen content in the lung tissue.

In this experimental example, analysis was performed using INSOLUBLE Collagen Assay (Biocolor, S2000). After sacrifice on the 21st day, the cryopreserved lung tissue was pulverized by adding 100 uL of Fragmentation Reagent, and then, 100 uL of 37% HCl was added and incubated at 65°C. for 3 hours. The contents of the tube were shaken at 30 minute intervals to aid tissue disintegration. After centrifugation, the concentration was adjusted to 100 μL and collagen staining was proceeded to prepare a sample. Absorbance was measured at 560 nm. The ratio value was measured by comparing the hydroxyproline value with a normal group, and the results are shown in Table 3 and FIG. 2.

TABLE 3

| | | Active component | | | Pirfenidone | Nintedanib |
|---|---|---|---|---|---|---|
| Nor-mal | Vehi-cle | 3 mg/kg | 10 mg/kg | 30 mg/kg | 200 mg/kg | 60 mg/kg |
| 96.11 | 260.33 | 253.56 | 217.22 | 171.33 | 177.44 | 239.78 |

From this experiment, it was confirmed that the content of collagen in the lung was significantly reduced at 10 and 30 mg/kg of 'active component' compared to Vehicle, which was a result similar to that of PID which is an existing SoC material. From this experiment, it can be seen that the degree of pulmonary fibrosis during administration of the active component was relieved.

Experimental Example 1-3: Histopathology (Ashcroft Score) Analysis

The degree of fibrosis and inflammation of the lung tissue were visually observed through a microscope, and the degree of fibrosis of lung tissue was measured with a Fibrotic Index according to normalized criteria. The higher the Fibrotic Index value, the more severe the degree and symptom of fibrosis. It is interpreted that as the value is lower, the symptom is relieved.

On the 21st day, lung tissue was separated and stained using H&E and MT stain, and observed at 200× magnification. The observed results were scored by Ashcroft (Hubner et al., 2008). The fibrotic index was calculated by dividing the sum of the adjusted Ashcroft field scores by the number of fields tested, and shown in Table 4 and FIG. 3.

TABLE 4

| Group | Number of individuals | Fibrotic Index (±SEM) |
|---|---|---|
| Normal | 9 | 0.1 (±0.1) |
| vehicle | 9 | 5.2 (±0.2) |
| Active component 3 mg/kg | 9 | 4.6 (±0.3) |
| Active component 10 mg/kg | 9 | 2.7 (±0.6) |
| Active component 30 mg/kg | 9 | 2.8 (±0.4) |
| Pirfenidone 200 mg/kg | 9 | 4.1 (±0.3) |
| Nintedanib 60 mg/kg | 9 | 3.1 (±0.6) |

In the case of 'active component' 10 and 30 mg/kg, tissue improvement effect equivalent to or greater than that of NIN was confirmed, and very excellent tissue improvement effect compared to PID was confirmed.

Experimental Example 1-4: Inflammation Cell Count Analysis

Since fibrosis is a chronic inflammatory disease characterized by excessive collagen deposition, the infiltration of inflammatory cells was analyzed to determine the degree of inflammation in the lung tissue.

At the sacrifice on the 21st day of administration, BALF (Bronchoalveolar lavage fluid) cells obtained through airway washing of mice were diluted with 1.05×PBS and attached to a slide, and then the slide was immersed and removed for 30 seconds in the order of 1, 2, 3 diff quick stain solution, and stained. It was counted based on 500 cells. Macrophages are the largest in size, mononuclear, and stained blue. Neutrophils and eosinophils form polynuclear cells, but eosinophils are stained red with eosin and distinguished from neutrophils. Lymphocytes have very less cytoplasm and are small in size as monocytes. The total cells were counted and converted into %, and shown in Table 5 and FIG. 4.

TABLE 5

| | Normal | Vehicle | Active component 3 mg/kg | Active component 10 mg/kg | Active component 30 mg/kg | Pirfenidone 200 mg/kg | Nintedanib 60 mg/kg |
|---|---|---|---|---|---|---|---|
| Macrophage | 0.42 | 6.96 | 7.80 | 5.60 | 4.91 | 5.01 | 5.61 |
| Neutrophil | 0.00 | 2.12 | 1.74 | 1.54 | 0.82 | 0.68 | 1.29 |
| Lymphocyte | 0.00 | 0.87 | 0.79 | 0.51 | 0.46 | 0.46 | 0.68 |
| Total cell | 0.42 | 9.93 | 10.32 | 7.66 | 6.19 | 6.14 | 7.57 |

Through this experiment, it can be seen that compared to Vehicle, the total cell level was improved by 20% or more at 10 mg/kg of 'active component' and by 30% or more at 30 mg/kg, thereby improving the inflammation of the lung tissue. In particular, it was confirmed that Neutrophil cells are inflammatory cells that show a high rate of lung fibrotic inflammation, and the number of these cells decreased by 20% or more at 10 mg/kg of 'active component' and by 60% or more at 30 mg/kg, compared to Vehicle, so that the ratio of major inflammatory cells was significantly improved. It can be seen that this is a level equivalent to PID which is an existing SoC material, and is superior effect to that of NIN.

Experimental Example 1-5: Measurement of Change in Body Weight

Body weight is an indirect indicator that can know the degree of improvement in the overall physical condition of the animal model. When the degree of weight loss is small, it can be inferred that the overall physical condition or symptoms of the disease are improved.

The body weight was measured using a scale on the 21st day when the administration was completed, and the results are shown in Table 6 and FIG. 5 below.

TABLE 6

| | | Active component | | | Pirfenidone | Nintedanib |
|---|---|---|---|---|---|---|
| Normal | Vehicle | 3 mg/kg | 10 mg/kg | 30 mg/kg | 200 mg/kg | 60 mg/kg |
| 13.22 | −23.33 | −22.44 | −19.11 | −16.78 | −14.67 | −19.44 |

It is confirmed that the degree of body weight loss is improved at 10 mg/kg and 30 mg/kg than in Vehicle group. This confirms that the effect is improved in a level similar to or greater than the SoC material, and the overall symptoms are improved when 'active component' is administered.

Through the above series of experimental results, it can be confirmed that when 'active component' was administered to mice at 10 mpk once a day, therapeutic effect is a level equivalent to the existing IPF standard of care.

Experimental Example 2: 2-Week Repeated Dose Toxicity Test in Mice

The active component was orally administered to acclimatized ICR mice for 7 days or more for 2 weeks. The composition of the experimental group is as shown in Table 7 below, and the body weight, general symptom observation, hematology/blood biochemical test, organ weight measurement, and histopathological tests were performed.

TABLE 7

| Group | Gender | Number of animals (number) | Dosing substance | Dosage (mg/kg/day) | Dosage amount (mL/kg/day) |
|---|---|---|---|---|---|
| G1 | M | 6 | Sterile distilled water | — | 10 |
| G2 | M | 6 | Active component | 30 | 10 |
| G3 | M | 6 | Active component | 60 | 10 |
| G4 | M | 6 | Active component | 120 → 90[1)] | 10 |

[1)]Confirmation of death individuals in the initial administration (within a few days after administration) of the high-dose group, or if the animal's condition is unlikely to last for 2 weeks, lower the dose and administer for the rest of the period.

After administration for 2 weeks, autopsies were performed on all animals. At autopsy, the weight of each organ was measured. No toxicity or significant abnormal symptoms were identified in all the results measured after repeated administration for 2 weeks. However, as shown in Table 8 below, in the administration group of 30 mg/kg/day or more, a slight weight loss tendency was observed only in the spleen and thymus among all organs.

TABLE 8

| | Dose (mg/kg) | | | |
|---|---|---|---|---|
| | 0 | 30 | 60 | 120→90 |
| SPLEEN | 0.080 ± 0.018 | 0.059 ± 0.011 | 0.070 ± 0.015 | 0.046 ± 0.021 |
| % to BODY WEIGHT | 0.28 ± 0.07 | 0.22 ± 0.04 | 0.25 ± 0.05 | 0.17 ± 0.08 |
| THYMUS | 0.034 ± 0.008 | 0.026 ± 0.008 | 0.029 ± 0.006 | 0.015 ± 0.012 |
| % to BODY WEIGHT | 0.12 ± 0.02 | 0.10 ± 0.03 | 0.11 ± 0.02 | 0.05 ± 0.04 |

Such results are considered to be independent of toxicity, but based on the weight loss tendency of the spleen and thymus, the active dose of the active component was set to 10 mg/kg to prevent potential risk of toxicity during long-term administration.

Experimental Example 3: Animal Pharmacokinetics/Pharmacodynamic Analysis

The pharmacokinetic test after a single oral administration of the active component in ICR mice proceeded as shown in Table 9 below. The pharmacokinetic parameters were calculated using Excel® and WinNonlin6.1 software for the blood drug concentration according to the change over time obtained through LC-MS/MS, and changes in the blood concentration of the active component are shown in Table 9 and FIG. 6.

TABLE 9

| | |
|---|---|
| Experimental animal | ICR mice (male) |
| Test material | Active component |
| Administration route | Oral |
| Number of administration | Single time |
| Dosage (mg/kg) | 10 |
| Dosing volume (mL/kg) | 10 |
| Blood collection time (hr) | 0.083, 0.25, 0.5, 1, 2, 4, 6, 8, 24 |
| Vehicle | saline |
| Number of test animals | 6 (n = 3, cross blood collection) |

TABLE 10

| Test material | Active component |
|---|---|
| Dosage (mg/kg) | 10 |
| $t_{1/2}$ (hr) | 2.50 ± 2.48 |
| $T_{max}$ (hr) | 2.67 ± 1.15 |
| $C_{max}$ (ug/mL) | 0.263 ± 0.032 |
| $AUC_{0-t}$ (hr · ug/mL) | 1.07 ± 0.21 |
| AUCinh (hr · ng/ml) | 1190 |

Preparation Example 1: Preparation of Enteric-Coated Capsules Containing Active Components Only the main components were filled into capsules by dose using Vcaps® enteric coated capsules without any additional excipients to the hydrochloride form of the active component.

Preparation Example 2: Preparation of Enteric-Coated Tablets Containing Active Component Microcrystalline cellulose, lactose hydrate, crospovidone, and magnesium stearate were mixed with the hydrochloride form of the active component, prepared into a plate-shaped compressed product using a dry granulator, and pulverized with an oscillator to prepare a dry granule. Microcrystalline cellulose, lactose hydrate, and magnesium stearate were further mixed with the granulated material, subjected to compression molding to prepare tablets, and enteric coating was carried out to complete the process.

Experimental Example 4: Human Pharmacokinetics/Pharmacodynamic Analysis

In order to confirm safety/tolerance/pK to the human body, as shown in Table 11, a randomized, double-blind, placebo-controlled trial was designed with a single administration and a gradual dose increase for 72 healthy adults. The formulation used in the clinical trial was prepared in the same manner as in Preparation Examples 1 and 2.

TABLE 11

| Category | Group | Active component | Formulation | Administration method |
|---|---|---|---|---|
| Single administration | SAD1 | 100 mg | Enteric coated capsules | Single oral administration on an empty stomach |
| | SAD2 | 300 mg | | |
| | SAD3 | 600 mg | | |
| | SAD4 | 500 mg | Enteric coated tablet | |
| Multiple administration | MAD1 | 25 mg | | Orally administrated on an empty stomach twice a day for 13 consecutive days, followed by single administration in the morning on the 14th day |
| | MAD2 | 50 mg | | |
| | MAD3 | 100 mg | | |
| | MAD4 | 200 mg | | |

As a result of the above clinical trial, no serious abnormal signs or side effects were confirmed.

As a result of confirming the pK for a single administration, as can be seen in Table 12 and FIG. 7 below, plasma maximal concentrations were recorded within 1.5 to 8 hours after administration, and the geometric mean half-life ranged from 6.91 hours to 9.90 hours, and the plasma concentrations increased in a dose proportional relationship.

TABLE 12

| Item (GCV %) | Active component 100 mg (N = 6) | Active component 300 mg (N = 6) | Active component 600 mg (N = 6) | Active component 500 mg (N = 6) |
|---|---|---|---|---|
| $C_{max}$ (ng/mL) | 123.96 (37.72) | 276.80 (66.21) | 213.43 (433.75) | 513.56 (41.27) |
| $t_{max}$ (h)* | 3.00 (1.50, 4.00) | 2.50 (1.50, 8.00) | 2.00 (1.50, 5.00) | 3.01 (0.50, 5.00) |
| $AUC_{0\text{-}last}$ (h * ng/ml) | 594.10 (61.23) | 1478.84 (48.07) | 1008.65 (625.00) | 2282.37 (54.92) |
| $AUC_{0\text{-}\infty}$ (h * ng/ml) | 639.07 (58.10) | 1525.99 (47.06) | 1922.64 (222.08) | 2339.20 (53.27) |
| $T_{1/2}$ (h) | 6.91 (39.98) | 8.33 (24.57) | 9.90 (71.50) | 7.80 (13.49) |
| Vz/F (L) | 1560.44 (34.98) | 2361.87 (41.96) | 4459.07 (84.14) | 2406.62 (48.04) |
| CL/F (L/h) | 156.48 (58.10) | 196.59 (47.06) | 312.07 (222.08) | 213.75 (53.27) |
| MRT (h) | 9.26 (33.69) | 9.75 (21.76) | 9.79 (25.60) | 9.57 (27.28) |

GCV % = Geometric coefficient of variation
Notes:
$t_{max}$ represented as median; min, max.

Additionally, as can be seen in Table 13 and FIG. 8, the 14th day pK confirmation result for multiple administration confirmed that the maximum plasma concentration was recorded within 1.5 to 5 hours at steady state after administration, the geometric mean half-life ranged from 4.4 hours to 12.35 hours, and the geometric mean dose interval in vivo exposure (AUCτ) ranged from 183.32-3012.35 h·ng/ml. It was confirmed that the plasma concentrations have a dose linear relationship within the dose range of 25 mg to 200 mg of active component.

TABLE 13

| Item (GCV %) | Active component 25 $mg^T$ (N = 6) | Active component 50 $mg^T$ (N = 6) | Active component 100 $mg^T$ (N = 6) | Active component 200 $mg^T$ (N = 6) |
|---|---|---|---|---|
| | Day 14 | | | |
| $C_{max, ss}$ (ng/ml) | 36.50 (66.19) | 102.61 (67.99) | 151.27 (65.36) | 595.35 (36.32) |
| $t_{max, ss}$ (h)* | 2.00 (1.50, 4.00) | 3.00 (3.00, 5.00) | 3.00 (1.50, 4.00) | 2.00 (1.50, 5.00) |
| $AUC_T$ (h * ng/ml) | 183.32 (76.35) | 429.09 (128.63) | 617.40 (60.53) | 3012.35 (48.42) |
| $AUC_{0\text{-}\infty}$ (h * ng/ml) | 300.73 (102.79) | 565.34 (232.53) | 887.97 (60.55) | 4747.29 (64.90) |
| $T_{1/2}$ (h) | 7.63 (46.84) | 4.40 (101.38) | 9.26 (22.69) | 12.35 (34.54) |
| $Vz/F_{ss}$ (L) | 1433.79 (61.75) | 738.97 (34.90) | 2163.04 (63.58) | 1182.53 (48.47) |
| $CL/F_{ss}$ (L/h) | 122.65 (79.49) | 116.53 (128.63) | 161.97 (60.53) | 66.39 (48.42) |

TABLE 13-continued

| Item (GCV %) | Active component 25 $mg^T$ (N = 6) | Active component 50 $mg^T$ (N = 6) | Active component 100 $mg^T$ (N = 6) | Active component 200 $mg^T$ (N = 6) |
|---|---|---|---|---|
| MRT (h) | 10.53 (31.65) | 8.44 (68.43) | 10.17 (9.35) | 12.07 (26.90) |
| Accumulation ratio based on $AUC_T$ | 1.94 (26.34) | 2.33 (31.42) | 1.88 (35.07) | 3.75 (36.01) |

Abbreviations:
GCV % = Geometric coefficient of variation;
n = Number of subjects;
SD = Standard Deviation;
T = Tablet.
Notes:
*$t_{max,\ ss}$ represented as median; min, max. MRT, $AUC_T$, $CL/F_{ss}$, and $Vz/F_{ss}$ are considering a 12 hour dosing interval.

Therefore, the optimal pharmacokinetic model parameters that can explain the changes in concentrations at all doses observed using Excel® and WinNonlin8.1 software were estimated for the blood drug concentration obtained in the human multidose clinical trial. The level of exposure in humans was predicted at various doses orally administered, and the main results are shown in Table 14 below.

TABLE 14

| | Dose (mg) | | | |
|---|---|---|---|---|
| Parameter | 50 | 100 | 150 | 200 |
| $T_{1/2}$ (h) | 9.753195 | 9.753195 | 9.753195 | 9.753195 |
| $T_{max}$ (h) | 2.803 | 2.803 | 2.803 | 2.803 |
| $C_{max}$ (ng/ml) | 38.271 | 76.5419 | 114.813 | 153.084 |
| CL/F (mL/hr) | 215856.7 | 215856.7 | 215856.7 | 215856.5 |
| Vd/F (mL) | 3037295 | 3037295 | 3037295 | 3037293 |
| $AUC_{tau}$ (hr * ng/ml) | 231.6352 | 463.2704 | 694.9055 | 926.5413 |
| $AUC_{tau}$_24 hr (hr * ng/ml) | 463.2704 | 926.5407 | 1389.811 | 1853.08256 |

From the mouse experimental model experiment for pulmonary fibrosis of Experimental Example 2, it was confirmed that administration of 10 mg/kg once a day is an effective dose for rats, and in Experimental Example 3, the rat plasma AUCinf value at the effective dose was 1190 hr·ng/ml. Therefore, in order to predict the dose expected to show an AUCinf value at the same level as the effective dose in rats in the human body, the correlation with AUC according to the administered dose was reviewed as shown in FIG. 9, and as a result, it was confirmed that 150 mg administration is necessary if it is intended to be administered to humans twice a day.

Experimental Example 5: Analysis of Human Administration Safety/Drug Tolerance The safety and drug resistance of the compound of the present invention during administration to humans was confirmed in the same manner as in Experimental Example 4.

As a result of confirming safety and tolerability for single administration, the most frequent adverse reactions were gastrointestinal adverse events including nausea, vomiting, diarrhea and abdominal pain. Among them, nausea and vomiting have been evaluated as having a significant impact on safety and drug resistance. It was confirmed that this was caused by the active component itself. As a result of confirming the relationship between the time of occurrence of these nausea and vomiting side effects and exposure to the body, as shown in FIG. 10, it has been confirmed that most of the occurrence occurs before the blood concentration in the body rises. It was found that the nausea and vomiting occurring during the administration of the active component acted on the gastrointestinal tract, exciting the vagus nerve, and thus activating the vomiting center, rather than the route of activation of the vomiting center through stimulation of the chemoreceptor-induced site by exposure to blood in the body.

Therefore, it can be seen that the method of administering an effective dose divided twice a day in order to reduce the rate of vagus nerve stimulation acting on the gastrointestinal tract is more appropriate for the active component.

Experimental Example 6: Confirmation of Human Therapeutic Effect

To confirm the safety and efficacy of the active component in patients with idiopathic pulmonary fibrosis, a randomized, double-blind, placebo-controlled trial was designed for standard-of-care treatment group or the non-treatment group as shown in Table 15. To confirm the safety and tolerability of the active component, after treatment of the active component for 24 weeks, it was evaluated in comparison with placebo. To confirm the therapeutic effect of the active component on idiopathic pulmonary fibrosis, after treatment of the active component for 24 weeks, the rate of reduction in forced vital capacity (FVC) from the base value for 24 weeks was evaluated as a primary efficacy evaluation variable after administration of the active component for 24 weeks. As a secondary validation variable, 1) respiratory-related mortality or hospitalization, acute deterioration of IPF, relative decrease in FVC value by 10% or more from the normal value, and time to IPF disease progression, including an absolute decrease in Hgb-corrected diffusing capacity for carbon monoxide (DLCO) value by 15% or more of the normal predicted value; 2) time required for unplanned first hospitalization for all causes during 24 weeks; 3) changes in functional motor ability compared to baseline as assessed by distance recording on the 6-minute walk test (6MWT) at week 24; 4) change in DLCO (corrected by Hgb) levels compared to baseline at week 24; 5) categorical assessment of absolute change in percent FVC predictive value compared to baseline at week 24; 6) change in quantitative chest high-resolution CT (HRCT) values compared to baseline at week 24; 7) changes in patient-reported outcomes (PRO) compared to baseline measured by St George's Respiratory Questionnaire, SGRQ, and Living with Idiopathic Pulmonary Fibrosis (L-IPF) at week 24, and the like, were evaluated. As an exploratory validity evaluation variable, 1) change in IPF-specific biomarkers compared to baseline at week 24; 2) changes in blood biomarkers compared to baseline at 24 weeks were evaluated. As safety evaluation variables, 1) incidence of abnormal reactions that occurred after administration of the active component; 2) physical examination; 3) 12 lead electrocardiogram; 4) signs of vitality; 5) clinical laboratory performance tests, and the like were evaluated.

The target group is divided into patients receiving Pirfenidone as an existing standard of care, patients receiving Nintedanib, and patients who have not received any treatment, and the effect resulting from administering the active component or a placebo to each patient group was confirmed. If an adverse reaction occurs due to the active component, the patient's response is closely monitored and the reduction of dose is considered.

TABLE 15

| Existing therapeutic agent | Active component 150 mg, BID | Active component 100 mg, BID | Placebo (0 mg), BID |
|---|---|---|---|
| Pirfenidone (mg, | 801 | 801 | 801 |
| administrated | 534 | 534 | 534 |
| 3 times a day) | 267 | 267 | 267 |
| | 600 | 600 | 600 |
| | 400 | 400 | 400 |
| | 200 | 200 | 200 |
| Nintedanib (mg, administrated | 150 | 150 | 150 |
| 2 times a day) | 100 | 100 | 100 |
| No therapeutic agent was administered (mg) | 0 | 0 | 0 |

The invention claimed is:

1. A method for treating fibrosis in a subject in need thereof, comprising administering to the subject 100 mg to 150 mg of a compound represented by the following Chemical Formula 1 or a pharmaceutically acceptable salt thereof twice a day (BID):

[Chemical Formula 1]

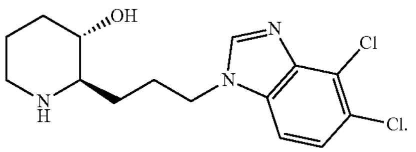

2. The method according to claim 1, wherein the fibrosis is Interstitial lung disease (ILD), Scleroderma, Keloid, Hypertrophic scar, Non-alcoholic Fatty Liver Disease, Primary sclerosing cholangitis (PSC), primary biliary cholangitis (PBC), diabetic retinopathy, Age-related Macular Degeneration (AMD), hypertrophic cardiomyopathy, myocardial infarction, Muscular Dystrophy, Diabetic kidney disease, focal segmental glomerulosclerosis (FSGS), or Inflammatory bowel disease (IBD).

3. The method according to claim 2, wherein the Interstitial lung disease (ILD) is idiopathic pulmonary fibrosis (IPF), systemic sclerosis associated interstitial lung disease (SSc-ILD), or chronic fibrosing interstitial lung diseases with a progressive phenotype (PF-ILD).

4. The method according to claim 1, wherein the pharmaceutically acceptable salt is hydrochloride.

5. The method according to claim 1, wherein the pharmaceutical composition further comprises other active component used for the prevention or treatment of fibrosis.

6. The method according to claim 5, wherein the other active component used for the prevention or treatment of fibrosis is Pirfenidone or Nintedanib.

* * * * *